United States Patent [19]

Brand et al.

[11] Patent Number: 4,467,096
[45] Date of Patent: Aug. 21, 1984

[54] ISOXAZOLYL INDOLAMINES

[75] Inventors: Leonard J. Brand, Randolph; Jeffrey Nadelson, Denville, both of N.J.

[73] Assignee: Sandoz, Inc., E. Hanover, N.J.

[21] Appl. No.: 525,248

[22] Filed: Aug. 22, 1983

Related U.S. Application Data

[62] Division of Ser. No. 359,752, Mar. 19, 1982, Pat. No. 4,421,752, which is a division of Ser. No. 251,068, Apr. 6, 1981, Pat. No. 4,336,391.

[51] Int. Cl.$^3$ .......................................... C07D 261/06
[52] U.S. Cl. ..................................... 548/247; 548/466; 548/493
[58] Field of Search ................................ 548/466, 247

[56] References Cited

U.S. PATENT DOCUMENTS 4,336,391  6/1982  Brand et al. .................. 548/247

FOREIGN PATENT DOCUMENTS 668506    7/1959   Canada ......................... 548/493
55-51505 11/1980   Japan .......................... 548/466

OTHER PUBLICATIONS

Shivarama et al., "Studies in Biheterocycles," *Indian J. Chem.*, vol. 16B, (1978), 240-1.

*Primary Examiner*—Donald G. Daus
*Assistant Examiner*—G. Hendricks
*Attorney, Agent, or Firm*—Gerald D. Sharkin; Robert S. Honor; Thomas O. McGovern

[57] ABSTRACT

This disclosure describes compounds of the formula

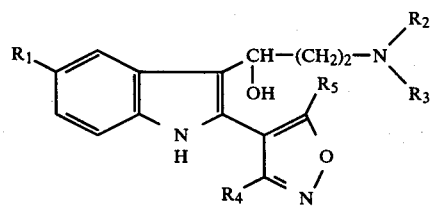

where
  $R_1$ represents hydrogen, fluoro, chloro, lower alkyl having 1 to 4 carbon atoms or lower alkoxy having 1 to 4 carbon atoms, and
  $R_2$ and $R_3$ each independently represent lower alkyl as defined above, or
  $R_2$ and $R_3$ together with N represent

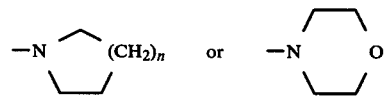

wherein
  n is 1, 2 or 3, and
  $R_4$ and $R_5$ each independently represent hydrogen or lower alkyl as defined above, or a pharmaceutically acceptable acid addition salt thereof, which are useful as anti-diabetic agents in particular as hypoglycemic agents and inhibiting or impeding post-prandial hyperglycemia.

2 Claims, No Drawings

ISOXAZOLYL INDOLAMINES

This is a division of application Ser. No. 359,752, filed Mar. 19, 1982, now U.S. Pat. No. 4,421,752 which in turn is a division of application Ser. No. 251,068, filed Apr. 6, 1981, now U.S. Pat. No. 4,336,391.

This invention relates to substituted indolamines which exhibit anti-diabetic activity. In particular, it relates to substituted isoxazolyl indolamines and pharmaceutically acceptable acid addition salts.

The compounds of this invention may be represented by the following structural formula:

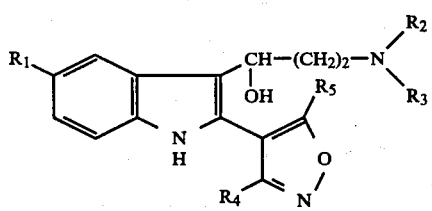

wherein
$R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like, and
$R_2$ and $R_3$ each independently represent lower alkyl as defined above, or
$R_2$ and $R_3$ together with N represent

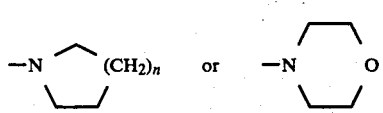

wherein
n is 1, 2 or 3, and
$R_4$ and $R_5$ each independently represent hydrogen or lower alkyl as defined above The compounds of formula (I), are prepared according to the following reaction scheme:

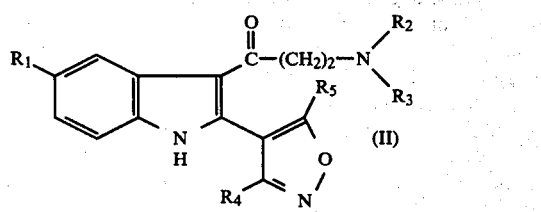

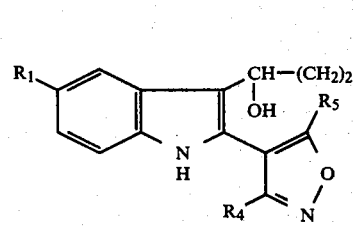

where $R_1$, $R_2$, $R_3$, $R_4$ and $R_5$ are as defined above.

The compounds of formula (I) are prepared by reducing a compound of the formula (II) with a reducing agent such as lithium aluminum hydride, or diborane, preferably lithium aluminum hydride. The reaction is carried out in the presence of an inert organic solvent, and although the particular solvent employed is not critical, the preferred solvents include an ether such as diethylether, dioxane or tetrahydrofuran, the latter being especially preferred. The temperature of the reaction may be critical, and it is preferred that the reaction be run at a temperature of from about $-10°$ to $+10°$ C., preferably 5° to 8° C. The reaction is run from about 1 to 7 hours, preferably from about 3 to 5 hours. The product is recovered using conventional techniques, e.g., crystallization.

The compounds of formula (II) are prepared according to the following reaction scheme:

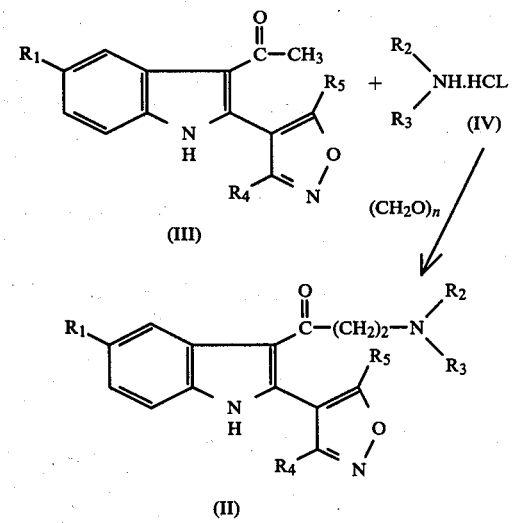

where
n is >3, and
$R_1$, $R_2$, $R_3$, $R_4$ and $R_5$ are as defined above.

The compounds of formula (II) are prepared by treating a compound of the formula (III) with a compound of the formula (IV) in the presence of an excess of paraformaldehyde and an organic solvent. Although the particular solvent employed is not critical, it is preferred that the reaction be run in the presence of the lower alkanols e.g., methanol, ethanol and the like, preferably ethanol. The temperature of the reaction is not critical but it is preferred that the reaction be run at a temperature of from about 60° to 150° C., preferably the reflux temperature of the solvent. The reaction is run from about 2 to 35 hours, preferably from about 20 to 30 hours. The product may be recovered by conventional techniques e.g., crystallization.

The compounds of formula (III) may be prepared in accordance with the following reaction scheme:

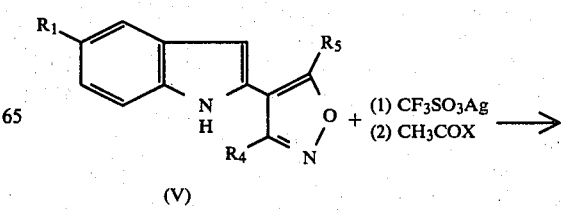

-continued

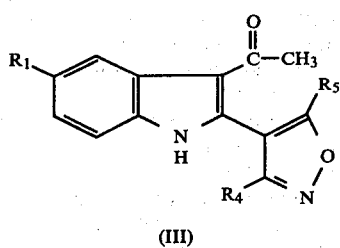

(III)

where
X is chloro or bromo, and
R₁, R₄ and R₅ are as defined above.

The compounds of formula (III) are prepared by reacting a compound of the formula (V) first with silver trifluoromethanesulfonate and then with an acetylhalide such as acetylchloride in the presence of an organic solvent. Although the particular solvent employed is not critical, the preferred solvents include the halogenated hydrocarbons such as methylene chloride, chloroform and the like preferably methylene chloride. The temperature of the reaction is not critical, but it is preferred that the reaction be run at a temperature of from about 20° to 45° C., preferably from about 25° to 35° C. The reaction is run from about 2 to 8 hours, preferably from about 3 to 6 hours. The product may be recovered by conventional techniques e.g., crystallization.

The compounds of formula (V) are prepared in accordance with the following reaction scheme:

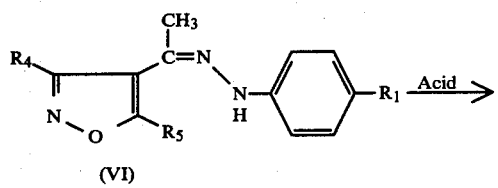

(VI)

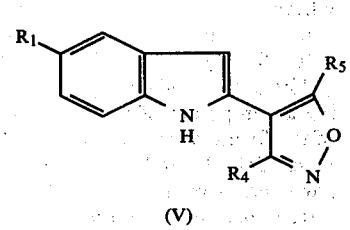

(V)

where R₁, R₄ and R₅ are as defined above.

The compounds of formula (V) are prepared by cyclizing a compound of the formula (VI) with an acid, such as acetic acid, p-toluenesulfonic acid or polyphosphoric acid, the latter being especially preferred in the presence of an inert solvent. Although the particular solvent employed is not critical, the preferred solvents include the aromatic hydrocarbons such as benzene, toluene and the like, or an excess of the acid utilized above, the latter being especially preferred. The temperature of the reaction is not critical, but it is preferred that the reaction be run from about 70° to 150° C., preferably from about 105° to 120° C. The reaction is run from about 1 to 12 hours, preferably from about 3 to 6 hours. The product is recovered using conventional techniques, e.g., filtration.

The compounds of formula (VI) are prepared according to the following reaction scheme:

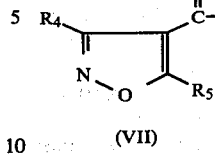 + 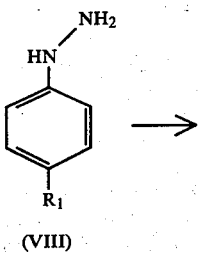

(VII)  (VIII)

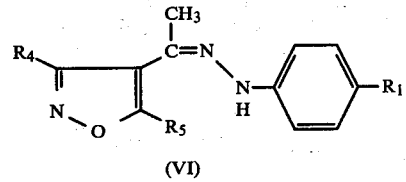

(VI)

where R₁, R₅ and R₆ are as defined above.

The compounds of formula (VI) are prepared by treating a compound of the formula (VII) with a compound of the formula (VIII) in the presence of an inert organic solvent and an acid catalyst such as p-toluenesulfonic acid, polyphosphoric acid or sulfuric acid, preferably p-toluenesulfonic acid. The particular solvent employed is not critical, but it is preferred that the reaction be run in the presence of the lower alkanols, e.g., methanol, ethanol and the like, or the aromatic hydrocarbons such as benzene, toluene and the like, preferably, however, ethanol. The temperature of the reaction is not critical, but it is preferred that the reaction be run from about 0° to 100° C., preferably from about 20° to 35° C. The reaction is run from about 12 to 72 hours, preferably from about 36 to 52 hours. The product is recovered using conventional techniques, e.g., filtration.

Many of the compounds of formulae (IV), (VII) and (VIII), are known and may be prepared by methods described in the literature. The compounds of formulae (IV), (VII) and (VIII) not specifically described may be prepared by analogous methods from known starting materials.

It will be understood that the compounds of formula (I) may exist in the form of optically active isomers and can be separated and recovered by conventional techniques, and that such isomeric forms are included within the scope of the invention.

The compounds of formula (I) and (II) and their pharmaceutically acceptable salts, are useful because they exhibit pharmacological activity in animals. In particular, the compounds of formula (I) and (II) are useful in the treatment of diabetes as hypoglycemic agents and inhibiting or impeding post-prandial hyperglycemia.

The compounds of formula (I) and (II) are useful in the treatment of diabetes as hypoglycemic agents as indicated by the lowering of blood glucose in 6 to 8 week old male Royal Hart mice weighing 30 to 35 grams which are fasted in groups of 5 for 16 hours and then are given an initial dose of 50 to 200 milligrams per kilogram of animal body weight of the compound orally. Two hours after the test compound is administered the mice are anesthetized with 85 milligrams per kilogram of animal body weight of sodium hexobarbital and five minutes later blood is collected via cardiac puncture. The blood samples are placed in an autoanalyzer cup containing 0.025 milliliters of heparin (1,000 units per milliliter); and the samples are capped, shaken and stored in ice. The glucose level is determined by the autoanalyzer potassium ferric cyanide N-2b method and these glucose levels are then compared with the glucose levels of the control group which receives orally 0.5% carboxymethyl cellulose and is run concurrently. To validate this experiment, a known hypoglycemic standard is included each time the test is run.

The compounds of formula (I) and (II) are also useful in treatment of diabetes by inhibiting or impeding postprandial hyperglycemia as indicated by a lowering of the blood sugar levels in male Wistar rats after an oral starch load. In this test male Wistar rats in groups of 5 which are fasted for 16 hours are given an initial dose of from 25 to 200 mg/kg p.o. of the test compound. One hour later the rats are given 1.0 grams per kilogram of animal body weight of cooked starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliters). The heparinized blood is used to determine the blood sugar level with an autoanalyzer. The blood sugar content is compared to the control group which receives 0.5% carboxymethyl cellulose and an oral starch load and are run concurrently.

For both the hypoglycemic and inhibiting post-prandial hyperglycemia use, the compounds of formula (I) and (II) and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and and alginic acid, binding agents, e.g., magnesium stearate, stearic acid and talc. The tablets may be uncoated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The hypoglycemic effective amount of active ingredient employed in the treatment of diabetes may vary depending on the particular compound employed, the mode of administration and the severity of the condition being treated. However, in general satisfactory results in the treatment of diabetes are obtained when a compound of formula (I) or a compound of the formula (II) is administered at a daily dosage of from about 5 milligrams to about 800 milligrams per kilogram of animal body weight, preferably given orally and in divided doses two to four times a day, or in sustained release form. For most large mammals, the total daily dosage is from about 70 milligrams to about 1000 milligrams. Unit dosage forms suitable for internal use comprise from about 17.5 milligrams to about 1000 milligrams, more usually 17.5 to 500 milligrams, of the active compound in intimate admixture with a solid or liquid, pharmaceutically acceptable carrier.

The effective amount of active ingredient for inhibiting post-prandial hyperglycemia employed in the treatment of diabetes may vary depending on the particular compound employed, the mode of administration and the severity of the condition being treated. However, in general satisfactory results in the treatment of diabetes are obtained when a compound of formula (I), or a compound of the formula (II), is administered at a daily dosage of from about 5 milligrams to about 80 milligrams per kilogram of animal body weight, preferably given orally and in divided doses two to four times a day, or in sustained release form. For most large mammals, the total daily dosage is from about 25 milligrams to about 1000 milligrams, preferably given at mealtime as conventional in treatments with substances having such activity, e.g., three times a day, particularly before a carbohydrate-rich meal.

The compounds of formula (I) and (II) may be similarly administered in the form of their non-toxic pharmaceutically acceptable acid addition salts. Such salts possess the same order of activity as the free base and are readily prepated by reacting the compound with a pharmaceutically acceptable acid by conventional techniques, and accordingly are included within the scope of this invention. Representative of the inorganic salts are the hydrochloride, hydrobromide, hydroiodide, phosphate (including hydrogen phosphate), metaphosphate, and sulfate (including hydrogen sulfate). Representative examples of the organic salts are the acetate, maleate, fumarate and the like.

Tablets and capsules containing the ingredients indicated below may be prepared by conventional techniques and are useful in treating diabetes, at a dose of one tablet or capsule, 2 to 4 times a day.

| Ingredients | Weight (mg.) tablet | capsule |
| --- | --- | --- |
| 3-dimethylamino-1-[2-(3-ethyl-5-methyl-4-isoxazolyl)-1H—indol-3-yl]-1-propanol | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 | 500 |

EXAMPLE 1

1-(3-ethyl-5-methyl-4-isoxazolyl)-1-ethanone phenyl hydrazone

A mixture of 61.1 g. (0.4 mole) of 4-acetyl-3-ethyl-5-methyl-isoxazole, 39.4 ml. (0.4 mole) of phenyl hydrazine and 500 mg. toluenesulfonic acid in 400 ml. ethanol is stirred at room temperature for 48 hours. The resulting solid is filtered and washed with cold ether to give 1-(3-ethyl-5-methyl-4-isoxazolyl)-1-ethanone phenyl hydrazone; m.p. 72° to 75° C.

Following the above procedure and using in place of 4-acetyl-3-ethyl-5-methyl isoxazole an equivalent amount of
- (a) 4-acetyl-3-ethyl-isoxazole
- (b) 4-acetyl-5-methyl-isoxazole
- (c) 4-acetyl-3,5-dimethyl-isoxazole there is obtained
- (a) 1-(3-ethyl-4-isoxazolyl)-1-ethanone phenyl hydrazone
- (b) 1-(5-methyl-4-isoxazolyl)-1-ethanone phenyl hydrazone, or
- (c) 1-(3,5-dimethyl-4-isoxazolyl)-1-ethanone phenyl hydrazone.

Again, following the above procedure and using in place of phenyl hydrazine an equivalent amount of
- (d) p-fluorophenyl hydrazine there is obtained
- (d) 1-(3-ethyl-5-methyl-4-isoxazolyl)-1-ethanone-p-fluorophenyl hydrazone.

Again, following the procedure set out in Example I and using in place of 4-acetyl-3-ethyl-5-methyl-isoxazole an equivalent amount of 4-acetyl-3,5-dimethylisoxazole; and using in place of phenyl hydrazine an equivalent amount of p-fluorophenyl hydrazine there is obtained
- (e) 1-(3,5-dimethyl-4-isoxazolyl)-1-ethanone-p-fluorophenyl hydrazone.

EXAMPLE 2

2-(3-ethyl-5-methyl-4-isoxazolyl)-indole

To 1350 grams of polyphosphoric acid at 100° to 110° C. there is added portionwise 74.5 g. (0.307 mole) of 1-(3-ethyl-5-methyl-4-isoxazolyl)-1-ethanone phenyl hydrazone while maintaining the temperature between 105° C. and 115° C. After addition is complete, the mixture is stirred at 100° to 110° C. for 3 hours. The mixture is then poured onto ice and water and the resulting gum extracted into methylene chloride. The methylene chloride is decolorized, dried over anhydrous magnesium sulfate, filtered and evaporated in vacuo to give 2-(3-ethyl-5-methyl-4-isoxazolyl)-indole.

Following the above procedure and using in place of 1-(3-ethyl-5-methyl-4-isoxazolyl)-1-ethanone phenyl hydrazone an equivalent amount of
- (a) 1-(3-ethyl-4-isoxazolyl)-1-ethanone phenyl hydrazone
- (b) 1-(5-methyl-4-isoxazolyl)-1-ethanone phenyl hydrazone
- (c) 1-(3,5-dimethyl-4-isoxazolyl)-1-ethanone phenyl hydrazone
- (d) 1-(3-ethyl-5-methyl-4-isoxazolyl)-1-ethanon-p-fluorophenyl hydrazone, or
- (e) 1-(3,5-dimethyl-4-isoxazolyl)-1-ethanone-p-fluorophenyl hydrazone there is obtained
- (a) 2-(3-ethyl-4-isoxazolyl)-indole,
- (b) 2-(5-methyl-4-isoxazolyl)-indole,
- (c) 2-(3,5-dimethyl-4-isoxazolyl)-indole
- (d) 5-fluoro-2-(3-ethyl-5-methyl-4-isoxazolyl)-indole, or
- (e) 5-fluoro-2-(3,5-dimethyl-4-isoxazolyl)-indole respectively.

EXAMPLE 3

2-(3-ethyl-5-methyl-4-isoxazolyl)-3-acetyl indole

[Compound II]

A solution of 33.5 g. (0.148 mole) of 2-(3-ethyl-5-methyl-4-isoxazolyl)-indole in 450 ml. methylene chloride is treated by the portionwise addition of 41.8 g. (0.163 mole) of silver trifluoromethanesulfonate. The resulting suspension is then treated by the dropwise addition of 12.8 g. (0.163 mole) of acetyl chloride in 50 ml. methylene chloride. The temperature rises to 35° C. during the addition. After the addition is complete the mixture is stirred at room temperature for 4 hours and then filtered. The filtrate is washed with 150 ml. 2N sodium hydroxide, water and 2N sodium hydroxide dried over anhydrous magnesium sulfate and evaporated in vacuo to given an oil. The oil is crystallized from ether to give 2-(3-ethyl-5-methyl-4-isoxazolyl)-3-acetyl indole, m.p. 170°–173° C.

Following the above procedure and using in place of 2-(3-ethyl-5-methyl-4-isoxazolyl)indole an equivalent amount of
- (a) 2-(3-ethyl-4-isoxazolyl)-indole,
- (b) 2-(5-methyl-4-isoxazolyl)-indole,
- (c) 2-(3,5-dimethyl-4-isoxazolyl)-indole
- (d) 5-fluoro-2-(3-ethyl-5-methyl-4-isoxazolyl)-indole, or
- (e) 5-fluoro-2-(3,5-dimethyl-4-isoxazolyl)-indole there is obtained
- (a) 2-(3-ethyl-4-isoxazolyl)-3-acetyl indole,
- (b) 2-(5-methyl-4-isoxazolyl)-3-acetyl indole,
- (c) 2-(3,5-dimethyl-4-isoxazolyl)-3-acetyl indole,
- (d) 5-fluoro-2-(3-ethyl-5-methyl-4-isoxazolyl)-3-acetyl indole, or
- (e) 5-fluoro-2-(3,5-dimethyl-4-isoxazolyl)-3-acetyl indole respectively.

EXAMPLE 4

[3-dimethylamino-1-[2-(3-ethyl-5-methyl-4-isoxazolyl)-1H-indol-3-yl]-1-propanone Compounds II]

A mixture of 12 g. (0.045 mole) of 2-(3-ethyl-5-methyl-4-isoxazolyl)-3-acetyl indole, 4 g. (0.049 mole) of dimethylamine hydrochloride, and 0.5 ml. concentrated hydrochloric acid in 70 ml. of ethanol is heated to reflux and treated by the portionwise addition of 14 g. (0.470 mole) of paraformaldehyde over 5 hours. The resulting mixture is refluxed an additional 24 hours, cooled and evaporated in vacuo. The residue is then dissolved in 300 ml. methylene chloride and washed with 200 ml. 2N hydrochloric acid, the aqueous acid is cooled and made basic with 2N sodium hydroxide and extracted with methylene chloride. The organic layer is dried over anhydrous magnesium sulfate, filtered and evaporated in vacuo. The residue is crystallized from ether to give 3-dimethylamino-1-[2-(3-ethyl-5-methyl-4-isoxazolyl)-1H-indol-3-yl]-1-propanone, m.p. 146°–148° C.

Following the above procedure and using in place of 2-(3-ethyl-5-methyl-4-isoxazolyl)-3-acetyl indole an equivalent amount of (a) 2-(3-ethyl-4-isoxazolyl)-3-acetyl indole,
(b) 2-(5-methyl-4-isoxazolyl)-3-acetyl indole,
(c) 3-(3,5-dimethyl-4-isoxazolyl)-3-acetyl indole,
(d) 5-fluoro-2-(3-ethyl-5-methyl-4-isoxazolyl)-3-acetyl indole, or
(e) 5-fluoro-2-(3,5-dimethyl-4-isoxazolyl)-3-acetyl indole there is obtained
(a) 3-dimethylamino-1-[2-(3-ethyl-4-isoxazolyl)-1H-indol-3-yl]-1-propanone
(b) 3-dimethylamino-1-[2-(5-methyl-4-isoxazolyl)-1H-indol-3-yl]-1-propanone
(c) 3-dimethylamino-1-[2-(3,5-dimethyl-4-isoxazolyl)-1H-indol-3-yl]-1-propanone
(d) 3-dimethylamino-1-[5-fluoro-2-(3-ethyl-5-methyl-4-isoxazolyl)-1H-indol-3-yl]-1-propanone, or
(e) 3-dimethylamino-1-[5-fluoro-2-(3,5-dimethyl-4-isoxazolyl)-1H-indol-3-yl]-1-propanone respectively.

Also following the above procedure and using in place of dimethylamine an equivalent amount of
(f) pyrrolidine
there is obtained
(f) 3-pyrrolidino-1-[2-(3-ethyl-5-methyl-4-isoxazolyl)-1H-indol-3-yl]-1-propanone.

The title compound of Example 4 has an ED$_{25}$ of 63.0 mg/kg in mice as a hypoglycemic agent.

EXAMPLE 5

3-dimethylamino-1-[2-(3-ethyl-5-methyl-4-isoxazolyl)-1H-indol-3-yl]-1-propanol

[Compounds I]

A suspension of 816 mg. (0.022 mole) of lithium aluminum hydride in 125 ml. tetrahydrofuran is cooled to 5° and treated by the dropwise addition of 3.5 g. (0.011 mole) of 3-dimethylamino-1-[2-(3-ethyl-5-methyl-4-isoxazolyl)-1H-indol-3-yl]-1-propanone in 125 ml. tetrahydrofuran maintaining the temperature between 5°-8° C. The resulting mixture is then stirred for 4 hours at 0°-5°, then cooled to −50° and quenched by the addition of 10 ml. saturated magnesium sulfate solution. The mixture is warmed to room temperature and filtered and the filtrate is evaporated in vacuo. The resulting residue is dissolved in methylene chloride, washed with water, dried over magnesium sulfate, filtered and evaporated in vacuo. The residue is crystallized from ether to give 3-dimethylamino-1-[2-(3-ethyl-5-methyl-4-isoxazolyl)-1H-indol-3-yl]-1-propanol, m.p. 166°-169° C.

Following the above procedure and using in place of 3-dimethylamino-1-[2-(3-ethyl-5-methyl-4-isoxazolyl)-1H-indol-3-yl]-1-propanone an equivalent amount of
(a) 3-dimethylamino-1-[2-(3-ethyl-4-isoxazolyl)-1H-indol-3-yl]-1-propanone
(b) 3-dimethylamino-1-[2-(5-methyl-4-isoxazolyl)-1H-indol-3-yl]-1-propanone
(c) 3-dimethylamino-1-[2-(3,5-dimethyl-4-isoxazolyl)-1H-indol-3-yl]-1-propanone
(d) 3-dimethylamino-1-[5-fluoro-2-(3-ethyl-5-methyl-4-isoxazolyl)-1H-indol-3-yl]-1-propanone
(e) 3-dimethylamino-1-[5-fluoro-2-(3,5-dimethyl-4-isoxazolyl)-1H-indol-3-yl]-1-propanone, or
(f) 3-pyrrolidino-1-[2-(3-ethyl-5-methyl-4-isoxazolyl)-1H-indol-3-yl]-1-propanone
there is obtained
(a) 3-dimethylamino-1-[2-(3-ethyl-4-isoxazolyl)-1H-indol-3-yl]-1-propanol
(b) 3-dimethylamino-1-[2-(5-methyl-4-isoxazolyl)-1H-indol-3-yl]-1-propanol
(c) 3-dimethylamino-1-[2-(3,5-dimethyl-4-isoxazolyl)-1H-indol-3-yl]-1-propanol
(d) 3-dimethylamino-1-[5-fluoro-2-(3-ethyl-5-methyl-4-isoxazolyl)-1H-indol-3-yl]-1-propanol
(e) 3-dimethylamino-1-[5-fluoro-2-(3,5-dimethyl-4-isoxazolyl)-1H-indol-3-yl]-1-propanol, or
(f) 3-pyrrolidino-1-[2-(3-ethyl-5-methyl-4-isoxazolyl)-1H-indol-3-yl]-1-propanol.

The title compound of Example 5 has an ED$_{25}$ of 83.0 mg/kg in mice as a hypoglycemic agent.

What is claimed is:
1. A compound of the formula

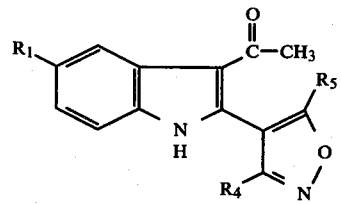

where $R_1$, represents hydrogen, fluoro, chloro, lower alkyl having 1 to 4 carbon atoms, or lower alkoxy having 1 to 4 carbon atoms, and $R_4$ and $R_5$ each independently represent hydrogen or lower alkyl having 1 to 4 carbon atoms.

2. The compound of claim 1, which is 2-(3-ethyl-5-methyl-4-isoxazolyl)-3-acetyl-indole.

* * * * *